United States Patent
Liu et al.

(10) Patent No.: US 11,009,479 B2
(45) Date of Patent: May 18, 2021

(54) SYSTEMS AND METHODS FOR THE DETECTION OF HBA1C

(71) Applicant: CASE WESTERN RESERVE UNIVERSITY, Cleveland, OH (US)

(72) Inventors: Chung Chiun Liu, Cleveland Heights, OH (US); Alireza Molazemhosseini, Milan (IT)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 230 days.

(21) Appl. No.: 15/973,218

(22) Filed: May 7, 2018

(65) Prior Publication Data

US 2018/0275090 A1    Sep. 27, 2018

Related U.S. Application Data

(63) Continuation-in-part of application No. PCT/US2018/025275, filed on Mar. 29, 2018, and a continuation-in-part of application No. 15/314,393, filed as application No. PCT/US2015/032609 on May 27, 2015, now Pat. No. 10,465,229, said application No. 15/973,218 is a continuation-in-part of application No. 15/314,380, filed as application No. (Continued)

(51) Int. Cl.
  *G01N 27/327*  (2006.01)
  *G01N 33/72*   (2006.01)
  *G01N 33/49*   (2006.01)

(52) U.S. Cl.
  CPC ..... *G01N 27/3277* (2013.01); *G01N 33/4915* (2013.01); *G01N 33/723* (2013.01); *G01N 2440/38* (2013.01); *G01N 2800/042* (2013.01)

(58) Field of Classification Search
  CPC .......... G01N 27/3277; G01N 33/4915; G01N 33/723; G01N 2440/38; G01N 2800/042
  See application file for complete search history.

(56) References Cited

U.S. PATENT DOCUMENTS

| 6,720,164 B1 | 4/2004 | Shinozuka et al. |
| RE40,198 E | 4/2008 | Buck, Jr. et al. |
| 2003/0155241 A1 | 8/2003 | Lai et al. |

(Continued)

FOREIGN PATENT DOCUMENTS

| EP | 2492351 A2 | 6/2018 |
| WO | 2003/040694 A2 | 5/2003 |

(Continued)

OTHER PUBLICATIONS

Q. Xue, et al. "An integrated micro immunosensor for hemoglobin-A1c level detection", In Proceedings of 2010 IEEE/ASME International Conference on Mechatronic and Embedded Systems and Applications, p. 208-212, Jul. 2010.*

(Continued)

*Primary Examiner* — J. Christopher Ball
(74) *Attorney, Agent, or Firm* — Tarolli, Sundheim, Covell & Tummino LLP

(57) ABSTRACT

A sensor for the detection of HbA1c in a sample includes a substrate, a working electrode and counter electrode formed on a surface of the substrate, and an anti-HbA1c antibody functionalized or chemically functionalized to a surface of an exposed portion of the working electrode.

17 Claims, 10 Drawing Sheets

Related U.S. Application Data

PCT/US2015/032399 on May 26, 2015, now Pat. No. 10,883,956.

(60) Provisional application No. 62/502,233, filed on May 5, 2017, provisional application No. 62/478,138, filed on Mar. 29, 2017, provisional application No. 62/084,188, filed on Nov. 25, 2014, provisional application No. 62/003,221, filed on May 27, 2014, provisional application No. 62/003,205, filed on May 27, 2014.

(56) References Cited

U.S. PATENT DOCUMENTS

| | | |
|---|---|---|
| 2004/0106190 A1 | 6/2004 | Yang et al. |
| 2004/0194302 A1 | 10/2004 | Bhullar et al. |
| 2005/0136500 A1 | 6/2005 | Yang et al. |
| 2006/0272958 A1 | 12/2006 | Lee |
| 2008/0027135 A1 | 1/2008 | Sondek et al. |
| 2008/0035180 A1 | 2/2008 | Mutharasan et al. |
| 2011/0055576 A1 | 3/2011 | Farrugia et al. |
| 2011/0210017 A1 | 9/2011 | Lai et al. |
| 2012/0046181 A1 | 2/2012 | Harb et al. |
| 2012/0061259 A1 | 3/2012 | Lin et al. |
| 2013/0065257 A1 | 3/2013 | Wang et al. |
| 2013/0203065 A1 | 8/2013 | Ettlinger et al. |
| 2014/0005068 A1 | 1/2014 | Das et al. |
| 2014/0011691 A1 | 1/2014 | Sierks et al. |
| 2014/0174950 A1 | 6/2014 | Gooding et al. |
| 2015/0047978 A1* | 2/2015 | Mathur .............. G01N 27/3271 204/403.14 |

FOREIGN PATENT DOCUMENTS

| | | |
|---|---|---|
| WO | 2004/021000 A1 | 3/2004 |
| WO | 2004/061418 A2 | 7/2004 |
| WO | 2014/032044 A1 | 2/2014 |

OTHER PUBLICATIONS

A. Chopra, et al. "Point-of-Car Amperometric Testing of Diabetic Marker (HbA1c) Using Specific Electroactive Antibodies", Electroanalysis, 26(3): p. 469-472, Mar. 2014.*

Office action for European Application No. 15799206.6-1118, dated May 8, 2018.

Chine Office action for Application No. 20158002310.7, dated Jun. 28, 2018.

Kim et al., "Impedometiric estrogen biosensor based on estrogen receptor alpha-immobilized gold electrode", Journal of Electroanalytical Chemistry, 671 (2012), pp. 106-111.

Shen, et al., "An iridium nanoparticles dispersed carbon based thick film electrochemical biosensor and its application or a single use, disposable glucose biosensor", Sensors and Actuators B, vol. 125 (2007) pp. 106-113.

Supplementary European Search Report for Application No. EP 15 79 9021, dated Sep. 14, 2017.

Dixon, Biochemical Education, 1975, 3(2):31-33.

Howell et al. Clin Chem., 1979, 25(2):269-272.

He Yahui, et al., "A New Optimized Spectrophotometric Assay for the Measurement of Pyruvate Dehydrogenase's Activity", Laboratory of Environmental Science, 2007, pp. 418-421.

Pushpa Sharma, el al., "Role of pyruvate dehydrogenase complex in traumatic brain injury and Measurement of pyruvate dehydrogenase enzyme by dipstick lest" J Emerg Trauma Shocll, May-Aug. 2009, 2(2): pp. 67-72.

K. Warriner, et al., "A lactate dehydrogenase amperometric pyruvate electrode exploiting direct detection of NAO+ at a poly(3-methylthiophene) :poly(phenol red) modified platinum surface", Materials Science and Engineering C 5 1997), pp. 91-99.

European Search Report for Application No. 15799206.6-1408 I3149466 PCT/US2015032609, dated Oct. 20, 2017.

Hinman et al. JBC, 1981, 256:6583-6586.

Q. Xue, et al. "An integrated micro immunosensor for hemoglobin-A1c level detection", In Pr5oceedings of 2010 IEEE/ASME International Conference on Mechatronic and Embedded Systems and Applications, p. 208-212, Jul. 2010.

First Named Inventor: Chung Chiun Liu; Title: System and Methods for the Detection of Biomarkers of Neurodegenerative Disorders; U.S. Appl. No. 15/970,738, filed May 3, 2018; Final Office Action; Notification Date: Sep. 22, 2020.

First Named Inventor: Chung Chiun Liu; Title: System and Methods for the Detection of Biomarkers of Glypican-1; U.S. Appl. No. 16/118,216, filed Aug. 30, 2018; Final Office Action; Notification Date: Oct. 8, 2020.

First Named Inventor: Chung Chiun Liu; Title: System and Method for Detecting Lysyl Oxidase-Like 2 Protein (LOXL2) and Breast Cancer; U.S. Appl. No. 16/168,630, filed Oct. 23, 2018; Office Action; Notification Date: Sep. 21, 2020; 7 pgs.

Karalemas et al., Talanta, 2000, 53:391-402.

Moreno-Bueno, et al., EMBO Mol Med., 2011, 3:528-544.

* cited by examiner

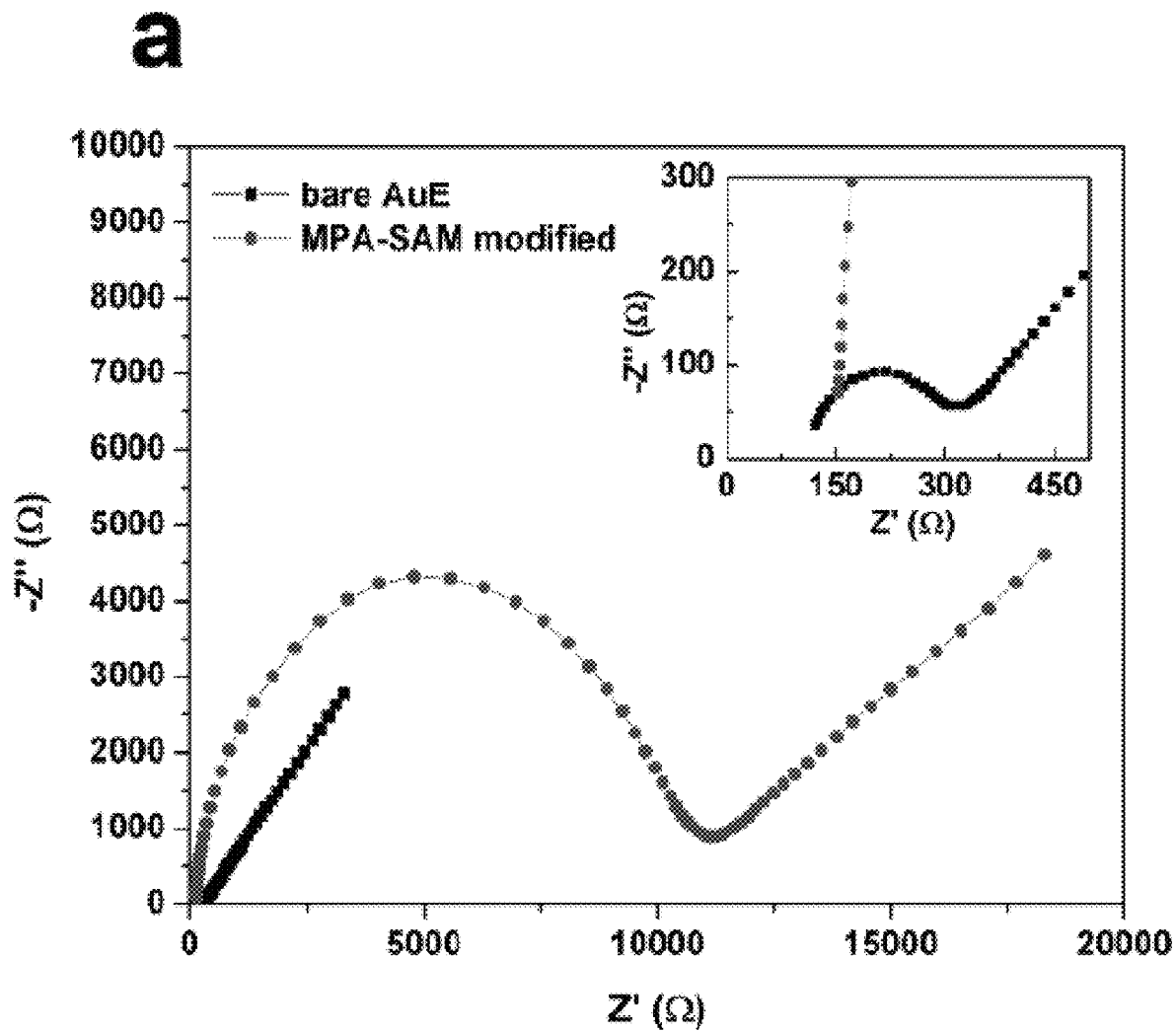
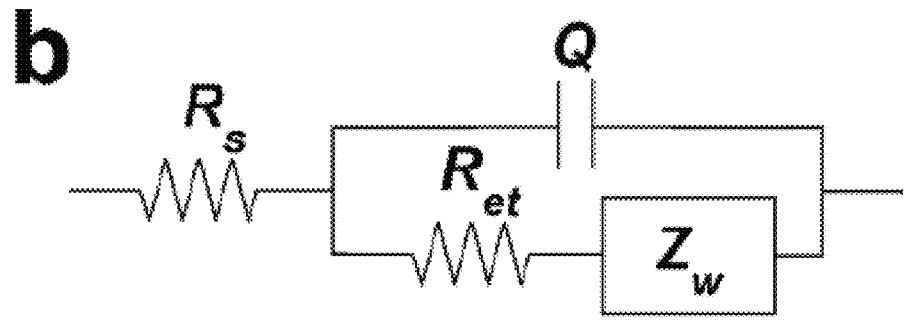
Figs. 6A-B

SYSTEMS AND METHODS FOR THE DETECTION OF HBA1C

RELATED APPLICATION

This application claims priority from U.S. Provisional Application No. 62/500,875, filed May 3, 2017, and is a Continuation-in-Part of PCT Application No. PCT/US2018/025275, filed Mar. 29, 2018, which claims priority to U.S. Provisional Application No. 62/478,138, filed Mar. 29, 2017, and is a Continuation-in-Part of U.S. application Ser. No. 15/314,393, filed Nov. 28, 2016, which is a National Phase filing of PCT/US2015/032609, filed May 27, 2015, which claims priority to U.S. Provisional Application No. 62/003,221, filed May 27, 2014, this application is also a Continuation-in-Part of U.S. Ser. No. 15/314,380, filed Nov. 28, 2016, which is a National Phase filing of PCT/US2015/032399, filed May 26, 2015, which claims priority to U.S. Ser. No. 62/003,205, filed May 27, 2014, and 62/084,188, filed Nov. 25, 2014, the subject matter of which are incorporated herein by reference in their entirety.

BACKGROUND

HbA1c is a stable glycosylated hemoglobin formed by the non-enzymatic reaction of glucose with the N-terminal valine of the β-chain of normal adult hemoglobin (HbA0). The HbA1c level is defined as the ratio between the HbA1c concentration and the total hemoglobin concentration. It is considered as a diagnostic biomarker for diabetic patients in addition to the measurement of the blood glucose level. The clinical reference range of HbA1c to the total hemoglobin (HbA0) is 5%-20%, and a value of 4%-6.5% is considered normal. The blood glucose level of a diabetic is not very stable, even over one single day, and thus the measurement of the HbA1c level can provide a more accurate indication of the glucose level in the blood over a time period of eight to 12 weeks. Therefore, the measurement of the HbA1c level is important for the long-term control of the glycemic state in diabetic patients.

HbA1C as the biomarker of diabetes can capture chronic hyperglycemia better than the oral glucose tolerance test (OGTT) or fasting plasma glucose (FPG) evaluation. Therefore, HbA1c can be a robust biomarker for both diagnosing and monitoring diabetes. On the other hand, arguments for defining diabetes by high blood glucose rather than by glycation of proteins persist. Also, the detection of HbA1c remains relatively costly. Thus, a cost-effective single-use disposable HbA1c biosensor that can measure the HbA1c level will be highly desirable for diabetic patient management.

There are clinical methods to analyze HbA1c including ion-exchange and boronated affinity chromatography, electrophoresis and fluorescence. However, these methods are relatively expensive, and require pretreatment of the blood sample, extensive analysis time and a skillful operator. Thus, a single-use disposable in vitro biosensor capable of the measurement of HbA1c with a suitable sensitivity and selectivity for diabetic management is scientifically and clinically significant. In addition to having the sensitivity and specificity of detecting HbA1c in a meaningful physiological range, it should require a small sample volume such as 10-15 µL of blood or other physiological fluids and it needs to have a fast response time, such as in seconds. Thus, this HbA1c biosensor can serve as a stand-alone monitoring system for HbA1c or as a part of a double diagnostic system for measuring the HbA1c and blood glucose simultaneously.

SUMMARY

Embodiments described herein relate to a detection system, method, and in vitro assay for detecting, identifying, quantifying, and/or determining the levels of HbA1c in a bodily sample as well as to a detection system, method, and in vitro assay for diagnosing, identifying, staging, and/or monitoring diabetes in a subject having or suspected of having diabetes.

In some embodiments, the system and/or method for detecting, identifying, quantifying, and/or determining diabetes can detect, identify, quantify, and/or determine the amount or level of HbA1c in a sample. The system can include an electrochemical biosensor, for detecting, identifying, quantifying, and/or determining the amount or level of HbA1c in a sample, such as blood. The system and method described herein can provide a single use, disposable, and cost-effective means for simple assessment of HbA1c in biological samples obtained by non-invasive or minimally invasive means.

In some embodiments, the system and methods described herein includes an electrochemical biosensor, a redox solution, and a measuring device. The electrochemical biosensor can produce a signal that is related to the presence or quantity of the HbA1c being detected in a sample. In some embodiments, the system can be used to detect and/or quantify HbA1c that is present in blood or a biological fluid.

In some embodiments, the electrochemical biosensor includes a substrate, a working electrode formed on a surface of the substrate and a counter electrode formed on the surface of the substrate. A dielectric layer covers a portion of the working electrode and counter electrode and defines an aperture exposing other portions of the working electrode and counter electrode. An anti-HbA1c antibody can be functionalized or chemically functionalized to a surface of an exposed portion of the working electrode. The anti-HbA1c antibody selectively binds to HbA1c in a sample, and the HbA1c once bound is detectable by measuring the current flow between the working electrode and counter electrode.

The redox solution is applied to the working electrode for determining the quantity of HbA1c in the sample bound to the anti-HbA1c antibody. The measuring device applies voltage potentials to the working electrode and counter electrode and measures the current flow between the working electrode and counter electrode to determine the level of the HbA1c in a sample, such as blood.

In some embodiments, the working electrode and the counter electrode include metalized films. The metalized films used to form the working electrode and the counter electrode can independently comprise gold, platinum, palladium, silver, carbon, alloys thereof, and composites thereof. The metalized films can be provided on the surface of the substrate by sputtering or coating the films on the surface and then laser ablating the films to form the working electrode and counter electrode.

In other embodiments, the sensor can include a reference electrode on the surface of the substrate. The dielectric can cover a portion of the reference electrode.

In other embodiments, the anti-HbA1c antibody can be chemically functionalized to the surface of the working electrode coated with a 3-mercaptopropionic acid (MPA) monolayer.

BRIEF DESCRIPTION OF THE DRAWINGS

FIGS. 6A-B illustrate (A) Nyquist plots obtained for the bare and MPA-SAM-covered AuEs in a frequency range of $10^{-2}$ to $10^4$ Hz; (B) Randles equivalent circuit used to model the experimental data.

DETAILED DESCRIPTION

Figure 1:
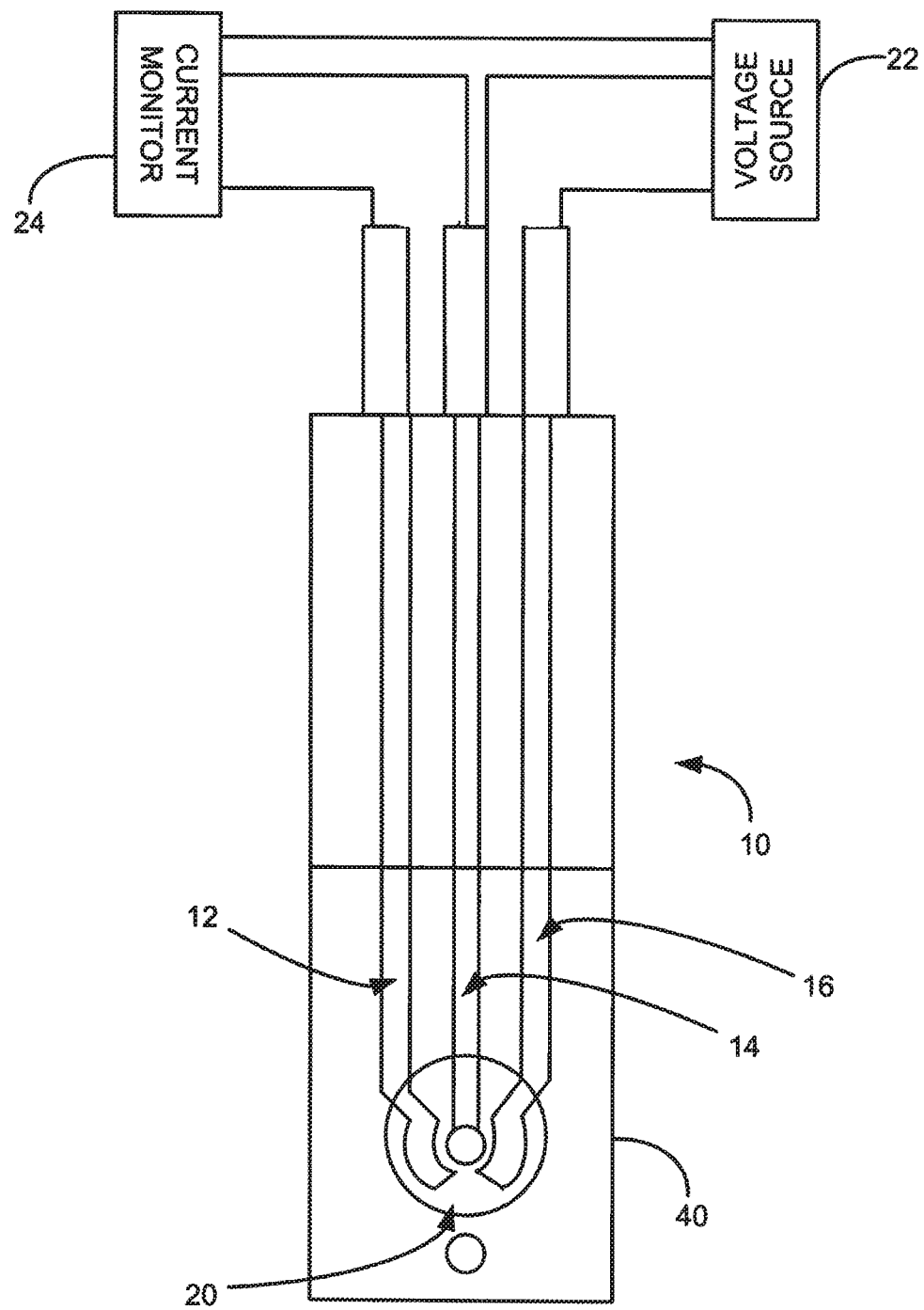
FIG. 1 is a schematic illustration of a biosensor in accordance with an aspect of the application.

Unless specifically addressed herein, all terms used have the same meaning as would be understood by those of skilled in the art of the subject matter of the application. The following definitions will provide clarity with respect to the terms used in the specification and claims.

As used herein, the term "monitoring" refers to the use of results generated from datasets to provide useful information about an individual or an individual's health or disease status. "Monitoring" can include, for example, determination of prognosis, risk-stratification, selection of drug therapy, assessment of ongoing drug therapy, determination of effectiveness of treatment, prediction of outcomes, determination of response to therapy, diagnosis of a disease or disease complication, following of progression of a disease or providing any information relating to a patient's health status over time, selecting patients most likely to benefit from experimental therapies with known molecular mechanisms of action, selecting patients most likely to benefit from approved drugs with known molecular mechanisms where that mechanism may be important in a small subset of a disease for which the medication may not have a label, screening a patient population to help decide on a more invasive/expensive test, for example, a cascade of tests from a non-invasive blood test to a more invasive option such as biopsy, or testing to assess side effects of drugs used to treat another indication.

As used herein, the term "quantitative data" or "quantitative level" or "quantitative amount" refers to data, levels, or amounts associated with any dataset components (e.g., markers, clinical indicia) that can be assigned a numerical value.

As used herein, the term "subject" refers to a human or another mammal. Typically, the terms "subject" and "patient" are used herein interchangeably in reference to a human individual.

As used herein, the term "bodily sample" refers to a sample that may be obtained from a subject (e.g., a human) or from components (e.g., tissues) of a subject. The sample may be of any biological tissue or fluid with, which analytes described herein may be assayed. Frequently, the sample will be a "clinical sample", i.e., a sample derived from a patient. Such samples include, but are not limited to, bodily fluids, e.g., saliva, breath, urine, blood, plasma, or sera; and archival samples with known diagnosis, treatment and/or outcome history. The term biological sample also encompasses any material derived by processing the bodily sample. Processing of the bodily sample may involve one or more of, filtration, distillation, extraction, concentration, inactivation of interfering components, addition of reagents, and the like.

As used herein, the terms "control" or "control sample" refer to one or more biological samples isolated from an individual or group of individuals that are normal (i.e., healthy). The term "control", "control value" or "control sample" can also refer to the compilation of data derived from samples of one or more individuals classified as normal.

As used herein, the terms "normal" and "healthy" are used interchangeably. They refer to an individual or group of individuals who have not shown any symptoms of diabetes, and have not been diagnosed with diabetes. In certain embodiments, normal individuals have similar sex, age, body mass index as compared with the individual from which the sample to be tested was obtained. The term "normal" is also used herein to qualify a sample isolated from a healthy individual.

As used herein, the terms "control" or "control sample" refer to one or more biological samples isolated from an individual or group of individuals that are normal (i.e., healthy). The term "control", "control value" or "control sample" can also refer to the compilation of data derived from samples of one or more individuals classified as normal, and/or one or more individuals diagnosed with diabetes.

As used herein, the term "indicative of diabetes", when applied to an amount of HbA1c in a bodily sample, refers to a level or an amount, which is diagnostic of diabetes such that the level or amount is found significantly more often in subjects with diabetes than in subjects without diabetes (as determined using routine statistical methods setting confidence levels at a minimum of 95%). Preferably, a level or amount, which is indicative of diabetes, is found in at least about 60% of subjects who have diabetes and is found in less than about 10% of subjects who do not have diabetes. More preferably, a level or amount, which is indicative of diabetes, is found in at least about 70%, at least about 75%, at least about 80%, at least about 85%, at least about 90%, at least about 95% or more in subjects who have diabetes and is found in less than about 10%, less than about 8%, less than about 5%, less than about 2.5%, or less than about 1% of subjects who do not have the diabetes.

Embodiments described herein relate to a detection system, method, and in vitro assay for detecting, identifying, quantifying, and/or determining the levels of HbA1c in a bodily sample as well as to a detection system, method, and in vitro assay for diagnosing, identifying, staging, and/or monitoring diabetes in a subject having or suspected of having diabetes.

In some embodiments, the system and/or method for detecting, identifying, quantifying, and/or determining diabetes can detect, identify, quantify, and/or determine the amount or level of HbA1c in a sample. The system can include an electrochemical biosensor, for detecting, identifying, quantifying, and/or determining the amount or level of HbA1c in a sample, such as blood. The system and method described herein can provide a single use, disposable, and cost-effective means for simple assessment of HbA1c in biological samples obtained by non-invasive or minimally invasive means.

In some embodiments, the electrochemical biosensor includes a substrate, a working electrode formed on a surface of the substrate and a counter electrode formed on the surface of the substrate. A dielectric layer covers a portion of the working electrode and counter electrode and defines an aperture exposing other portions of the working electrode and counter electrode. An anti-HbA1c antibody is functionalized or chemically functionalized to a surface of the exposed portion of the working electrode. The anti-HbA1c antibody selectively binds to HbA1c in a sample, and the HbA1c once bound is detectable by measuring the current flow between the working electrode and counter electrode.

The redox solution is applied to the working electrode for determining the quantity of HbA1c in the sample bound to the anti-HbA1c antibody. The measuring device applies voltage potentials to the working electrode and counter electrode and measures the current flow between the working electrode and counter electrode to determine the level of the HbA1c in a bodily sample, such as a blood.

The bio-recognition mechanism of this sensor is based on the influence of the redox coupling reaction of the redox solution, such as a potassium ferrocyanide/potassium ferricyanide ($K_3Fe(CN)_6/K_4Fe(CN)_6$) solution, by HbA1c and its receptor (anti-HbA1c antibody). In the detection of HbA1c, the anti-HbA1c antibody is used to provide a lock-and-key bio-recognition mechanism. The HbA1c interacts with the anti-HbA1c antibody affecting the electron charge transfer and can influence a redox coupling reaction in the redox solution applied to the working electrode. The level of HbA1c bound to the anti-HbA1c antibody can be determined by measuring current flow between the working and counter electrode to which the sample and redox solution has been applied and comparing the measured current to a control value, which can be based on a measured current between the working electrode and counter electrode that is free of bound anti-HbA1c antibody.

Differential pulse voltammetry (DPV) can employed as the transduction mechanism of this biosensor to determine the level of bound HbA1c. DPV applies a linear sweep voltammetry with a series of regular voltage pulses superimposed on the linear potential sweep. The current can then measured immediately before each potential change. Thus, the effect of the charging current could be minimized, achieving a higher sensitivity.

FIG. 1 illustrates a biosensor 10 of the system in accordance with an embodiment of the application. The sensor 10 is a three-electrode sensor including a counter electrode 12, a working electrode 14, and a reference electrode 16 that are formed on a surface of a substrate. A dielectric layer 40 covers a portion of the working electrode 12, counter electrode 14 and reference electrode 16. The dielectric layer 40 includes an aperture 20 that defines a detection region of the working electrode 12, counter electrode 14, and reference electrode 16, which is exposed to samples containing HbA1c to be detected. An anti-HbA1c antibody can be functionalized or chemically functionalized to the working electrode. The anti-HbA1c antibody can bind selectively to HbA1c in the biological sample.

The system further includes a measuring device that includes a voltage source 22 for applying a voltage potential to the working electrode, counter electrode, and/or reference electrode and a current monitor 24 for measuring the current flow between the working electrode and counter electrode.

The interaction of the anti-HbA1c antibody and HbA1c in the presence of a redox solution can be detected using electrochemical analytical techniques, such as cyclic voltammetry (CV), differential pulse voltammetry (DPV), to determine the presence of the analyte in the sample. The working electrode 14 is poised at an appropriate electrochemical potential such that the current that flows through the electrode changes when the anti-HbA1c antibody binds to HbA1c in the sample in the presence of the redox solution. The function of the counter electrode 12 is to complete the circuit, allowing charge to flow through the sensor 10.

The working electrode 14 and the counter electrode 12 are preferably formed of the same material, although this is not a requirement. Examples of materials that can be used for the working electrode 14 and counter electrode 12 include, but are not limited to, gold, platinum, palladium, silver, carbon, alloys thereof, and composites thereof.

The anti-HbA1c antibody, which is functionalized or chemically functionalized to the working electrode, can be an antibody that binds selectively to HbA1c. An antibody that binds selectively to HbA1c can be a monoclonal or polyclonal anti-HbA1c antibody that binds selectively or specifically to HbA1c. An anti-HbA1c antibody having binding affinities in the picomolar to micromolar range are suitable. Such interaction can be reversible or irreversible.

The term "functionalized" or "chemically functionalized," as used herein, means addition of functional groups onto the surface of a material by chemical reaction(s). As will be readily appreciated by a person skilled in the art, functionalization can be employed for surface modification of materials in order to achieve desired surface properties, such as biocompatibility, wettability, and so on. Similarly, the term "biofunctionalization," "biofunctionalized," or the like, as used herein, means modification of the surface of a material so that it has desired biological function, which will be readily appreciated by a person of skill in the related art, such as bioengineering.

The anti-HbA1c antibody may be functionalized to the working electrode covalently or non-covalently. Covalent attachment of an anti-HbA1c antibody to the working electrode may be direct or indirect (e.g., through a linker). Anti-HbA1c antibody may be immobilized on the working electrode using a linker. The linker can be a linker that can be used to link a variety of entities.

In some embodiments, the linker may be a homo-bifunctional linker or a hetero-bifunctional linker, depending upon the nature of the molecules to be conjugated. Homo-bifunctional linkers have two identical reactive groups. Hetero-bifunctional linkers have two different reactive groups. Various types of commercially available linkers are reactive with one or more of the following groups: primary amines, secondary amines, sulphydryls, carboxyls, carbonyls and carbohydrates. Examples of amine-specific linkers are N-hydroxysuccinimide (NHS), bis(sulfosuccinimidyl) suberate, bis[2-(succinimidooxycarbonyloxy)ethyl]sulfone, disuccinimidyl suberate, disuccinimidyl tartarate, N-succinimidyl S-acetylthioacetate, dimethyl adipimate 2HCl, dimethyl pimelimidate 2HCl, dimethyl suberimidate HCl, ethylene glycolbis-[succinimidyl-[succinate]], dithiolbis(succinimidyl propionate), and 3,3'-dithiobis(sulfosuccinimidylpropionate). Linkers reactive with sulfhydryl groups include bismaleimidohexane, 1,4-di-[3'-(2'-pyridyldithio)-propionamido)]butane, 1-[p-azidosalicylamido]-4-[iodoacetamido]butane, and N-[4-(p-azidosalicylamido)butyl]-3'-[2'-pyridyldithio]propionamide Linkers preferentially reactive with carbohydrates include azidobenzoyl hydrazine. Linkers preferentially reactive with carboxyl groups include 4[p-azidosalicylamido]butylamine.

Heterobifunctional linkers that react with amines and sulfhydryls include N-succinimidyl-3-[2-pyridyldithio]propionate, succinimidyl[4-iodoacetyl]aminobenzoate, succinimidyl 4-[N-maleimidomethyl]cyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-[N-maleimidomethyl]cyclohexane-1-carboxylate. Heterobifunctional linkers that react with carboxyl and amine groups include 1-ethyl-3-[3-dimethylaminopropyl]-carbodiimide hydrochloride. Heterobifunctional linkers that react with carbohydrates and sulfhydryls include 4-[N-maleimidomethyl]-cyclohexane-1-carboxyl-hydrazide HCl, 4-(4-N-maleimidophenyl)-butyric acid hydrazide 2HCl, and 3-[2-pyridyldithio]propionyl hydrazide.

Alternatively, anti-HbA1c antibodies may be non-covalently coated onto the working electrode. Non-covalent deposition of the anti-HbA1c antibody to the working electrode may involve the use of a polymer matrix. The polymer may be naturally occurring or non-naturally occurring and may be of any type including but not limited to nucleic acid (e.g., DNA, RNA, PNA, LNA, and the like, or mimics, derivatives, or combinations thereof), amino acids (e.g., peptides, proteins (native or denatured), and the like, or mimics, derivatives, or combinations thereof, lipids, polysaccharides, and functionalized block copolymers. The anti-HbA1c antibody may be adsorbed onto and/or entrapped within the polymer matrix.

Alternatively, the anti-HbA1c antibody may be covalently conjugated or crosslinked to the polymer (e.g., it may be "grafted" onto a functionalized polymer).

An example of a suitable peptide polymer is poly-lysine (e.g., poly-L-lysine). Examples of other polymers include block copolymers that comprise polyethylene glycol (PEG), polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes, alkyl cellulose, hydroxyalkyl celluloses, cellulose ethers, cellulose esters, nitrocelluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, polyvinyl chloride, polystyrene, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly (octadecyl acrylate), poly(lactide-glycolide), copolyoxalates, polycaprolactones, polyesteramides, polyorthoesters, polyhydroxybutyric acid, polyanhydrides, poly(styrene-b-isobutylene-b-styrene) (SIBS) block copolymer, ethylene vinyl acetate, poly(meth)acrylic acid, polymers of lactic acid and glycolic acid, polyanhydrides, poly(ortho)esters, polyurethanes, poly(butic acid), poly(valeric acid), and poly (lactide-cocaprolactone), and natural polymers such as alginate and other polysaccharides including dextran and cellulose, collagen, albumin and other hydrophilic proteins, and other prolamines and hydrophobic proteins, copolymers and mixtures thereof, and chemical derivatives thereof including substitutions and/or additions of chemical groups, for example, alkyl, alkylene, hydroxylations, oxidations, and other modifications routinely made by those skilled in the art.

In one particular embodiment, the working electrode can comprise a gold working electrode that is coated with a self-assembled monolayer (SAM) of 3-mercaptopropionic acid (MPA). The MPA molecule includes a thiol functional group at one end with an affinity for gold and a carboxylic group at the other end, which can covalently bond to proteins through a peptide bond after activation. The SAM of MPT can be activated by reaction with N-(3-dimethylaminopropyl)-N'-ethylcarbodiimide hydrochloride (EDC) and N-hydroxysuccinimide (NHS), which can further react with amine groups of proteins and antibodies.

In some embodiments, the anti-HbA1c antibody can include monoclonal and polyclonal antibodies, immunologically active fragments (e.g., Fab or (Fab)2 fragments), antibody heavy chains, humanized antibodies, antibody light chains, and chimeric antibodies. Anti-HbA1c antibody, including monoclonal and polyclonal antibodies, fragments and chimeras, may be prepared using methods known in the art (see, for example, R. G. Mage and E Lamoyi, in "Monoclonal Antibody Production Techniques and Applications", 1987, Marcel Dekker, Inc.: New York, pp. 79-97; G. Kohler and C. Milstein, Nature, 1975, 256: 495-497; D. Kozbor et al., J. Immunol. Methods, 1985, 81: 31-42; and R. J. Cote et al., Proc. Natl. Acad. Sci. 1983, 80: 2026-203; R. A. Lerner, Nature, 1982, 299: 593-596; A. C. Nairn et al., Nature, 1982, 299: 734-736; A. J. Czernik et al., Methods Enzymol. 1991, 201: 264-283; A. J. Czernik et al., Neuromethods: Regulatory Protein Modification: Techniques & Protocols, 1997, 30: 219-250; A. J. Czemik et al., NeuroNeuroprotocols, 1995, 6: 56-61; H. Zhang et al., J. Biol. Chern. 2002, 277: 39379-39387; S. L. Morrison et al., Proc. Natl. Acad. Sci., 1984, 81: 6851-6855; M. S. Neuberger et al., Nature, 1984, 312: 604-608; S. Takeda et al., Nature, 1985, 314: 452-454). Antibodies to be used in the biosensor can be purified by methods well known in the art (see, for example, S. A. Minden, "Monoclonal Antibody Purification", 1996, IBC Biomedical Library Series: Southbridge, Mass.). For example, anti-HbA1c antibodies can be affinity purified by passage over a column to which a protein marker or fragment thereof is bound. The bound antibodies can then be eluted from the column using a buffer with a high salt concentration.

Instead of being prepared, anti-HbA1c antibodies to be used in the methods described herein may be obtained from scientific or commercial sources.

In order to minimize any non-specific binding on the working electrode surface and blocking any open surface area of the working electrode at least one blocking agent can be applied to the surface of the working electrode once the anti-HbA1c antibody has been functionalized or chemically functionalized to the working electrode. The blocking agent can enhance the reproducibility and sensitivity of the biosensor by minimizing non-specific interactions on the working electrode. In some embodiments, the blocking agent can include dithiothreitol or casein. The blocking agent can be applied to the surface of the working at an amount effective to minimize non-specific binding of proteins or other molecules on the surface of the working electrode.

The redox solution is applied to the working electrode for determining the quantity of HbA1c in the sample bound to the anti-HbA1c antibody. The redox coupling solution can include a redox mediator, such as potassium ferrocyanide/potassium ferricyanide ($K_3Fe(CN)_6/K_4Fe(CN)_6$), that is provided at equimolar concentration in a PBS solution.

The voltage source 22 can apply a voltage potential to the working electrode 14 and reference and/or counter electrode 16, 12, depending on the design of the sensor 10. The current between the working electrode 14 and counter electrode 16 can be measured with the measuring device or meter 24. Such current is dependent on interaction of HbA1c in the sample with the anti-HbA1c antibody on the working electrode.

The amount or level of current measured is proportional to the level or amount of HbA1c in the sample. In some embodiments, where the sample is blood, once the current level generated by the sample and redox solution tested with the sensor is determined, the level can be compared to a predetermined value or control value to provide information for monitoring the presence or absence of HbA1c in the blood sample.

In other embodiments, where the sample is a bodily sample obtained from a subject, once the current level generated by the reaction solution tested with the sensor is determined, the level can be compared to a predetermined value or control value to provide information for diagnosing or monitoring of the condition, pathology, or disorder in a subject that is associated with presence or absence of HbA1c, such as diabetes.

The current level generated by sample obtained from the subject can be compared to a current level of a sample previously obtained from the subject, such as prior to administration of a therapeutic. Accordingly, the methods described herein can be used to measure the efficacy of a therapeutic regimen for the treatment of a condition, pathology, or disorder associated with the level of the HbA1c in a subject by comparing the current level obtained before and after a therapeutic regimen. Additionally, the methods described herein can be used to measure the progression of a condition, pathology, or disorder associated with the presence or absence of the HbA1c in a subject by comparing the current level in a bodily sample obtained over a given time period, such as days, weeks, months, or years.

The current level generated by a sample obtained from a subject may also be compared to a predetermined value or control value to provide information for determining the severity or aggressiveness of a condition, pathology, or disorder associated with HbA1c levels in the subject. A predetermined value or control value can be based upon the current level in comparable samples obtained from a healthy or normal subject or the general population or from a select population of control subjects.

The predetermined value can take a variety of forms. The predetermined value can be a single cut-off value, such as a median or mean. The predetermined value can be established based upon comparative groups such as where the current level in one defined group is double the current level in another defined group. The predetermined value can be a range, for example, where the general subject population is divided equally (or unequally) into groups, or into quadrants, the lowest quadrant being subjects with the lowest current level, the highest quadrant being individuals with the highest current level. In an exemplary embodiment, two cutoff values are selected to minimize the rate of false positive and negative results.

The biosensor illustrated in FIG. 1 can be fabricated on a substrate 100 formed from polyester or other electrically non-conductive material, such as other polymeric materials, alumina ($Al_2O_3$), ceramic based materials, glass or a semi-conductive substrate, such as silicon, silicon oxide and other covered substrates. Multiple sensor devices can thus be formed on a common substrate. As will be appreciated, variations in the geometry and size of the electrodes are contemplated.

The biosensor can be made using a thin film, thick film, and/or ink-jet printing technique, especially for the deposition of multiple electrodes on a substrate. The thin film process can include physical or chemical vapor deposition. Electrochemical sensors and thick film techniques for their fabrication are discussed in U.S. Pat. No. 4,571,292 to C. C. Liu et al., U.S. Pat. No. 4,655,880 to C. C. Liu, and co-pending application U.S. Ser. No. 09/466,865, which are incorporated by reference in their entirety.

In some embodiments, the working electrode, counter electrode, and reference electrode may be formed using laser ablation, a process which can produce elements with features that are less than one-thousandth of an inch. Laser ablation enables the precise definition of the working electrode, counter electrode, and reference electrode as well as electrical connecting leads and other features, which is required to reduce coefficient of variation and provide accurate measurements. Metalized films, such as Au, Pd, and Pt or any metal having similar electrochemical properties, that can be sputtered or coated on plastic substrates, such as PET or polycarbonate, or other dielectric material, can be irradiated using laser ablation to provide these features.

In one example, a gold film with a thickness of about 300 Å to about 2000 Å can be deposited by a sputtering technique resulting in very uniform layer that can be laser ablated to form the working and counter electrodes. The counter electrode can use other materials. However, for the simplicity of fabrication, using identical material for both working and counter electrodes will simplify the fabrication process providing the feasibility of producing both electrodes in a single processing step. An Ag/AgCl reference electrode, the insulation layer, and the electrical connecting parts can then be printed using thick-film screen printing techniques.

The working electrode surface can then be cross-linked or biotinylated chemically in order to allow the attachment of an anti-HbA1c antibody. The crosslinking step can be accomplished by generating thiol bonds. This can be chemically accomplished using, for example, a self-assembled monolayer (SAM) of 3-mercaptopropionic acid (MPA). The MPA molecule includes a thiol functional group at one end with an affinity for gold and a carboxylic group at the other end, which can covalently bond to proteins through peptide bond after activation. The SAM of MPT can be activated for binding to a protein, such as an antibody, by reaction with N-(3-dimethylaminopropyl)-N'-ethylcarbodiimide hydrochloride (EDC) and N-hydroxysuccinimide (NHS) that can further react with amine groups of proteins and antibodies. Similar chemical methods can be used to produce semi-stable amine-ester groups to enhance the cross linking between the antibodies and the thiol groups. Other cross-linking agent, such as 3,3'-dithiobis[sulfosuccinimidylpropionate] (DTSSP), can also be used in this process.

Biotinylation is rapid, specific and is normally unperturb to the natural function of the molecule due to the relatively small size of biotin. Streptavidin and similar chemicals such as avidin can be immobilized on the working electrode surface for a biosensor for the detection of an interaction of anti-HbA1c antibody and HbA1c.

Following addition of an anti-HbA1c antibody to the working electrode, the working electrode surface can be blocked using a blocking agent to minimize any non-specific molecule (e.g., protein) bonding on the electrode surface. This step will enhance the reproducibility and sensitivity of the biosensor. In some embodiments, DTT (Dithiothreitol), casein, and/or other blocking agents can be used to cover the open surface area of the working electrode and minimize any non-specific protein coverage.

In other embodiments, a plurality of biosensors can be provided on a surface of a substrate to provide a biosensor array. The biosensor array can be configured to HbA1c concentration changes in a host of chemical and/or biological processes occurring in proximity to the array. The biosensor array can include a plurality biosensors arranged in a plurality of rows and a plurality of columns. Each biosensor can use a working electrode, a counter electrode, and a dielectric layer covering a portion of the working electrode and counter electrode and defining an aperture exposing other portions of the working electrode and counter electrode. Anti-HbA1c antibodies for HbA1c can be functionalized or chemically functionalized to the working electrode. The anti-HbA1c antibodies can be the same or different for each biosensor of the array and can bind selectively to HbA1c. The biosensors of the array can be configured to provide at least one output signal representing the presence and/or concentration of HbA1c proximate to a surface of the array. For each column of the plurality of columns or for each row of the plurality of rows, the array further comprises column or row circuitry configured to provide voltage potentials to respective biosensors in the column or row. Each biosensor in the row or column can potentially detect a different analyte and/or biased to detect different analytes.

Example

Figure 2:
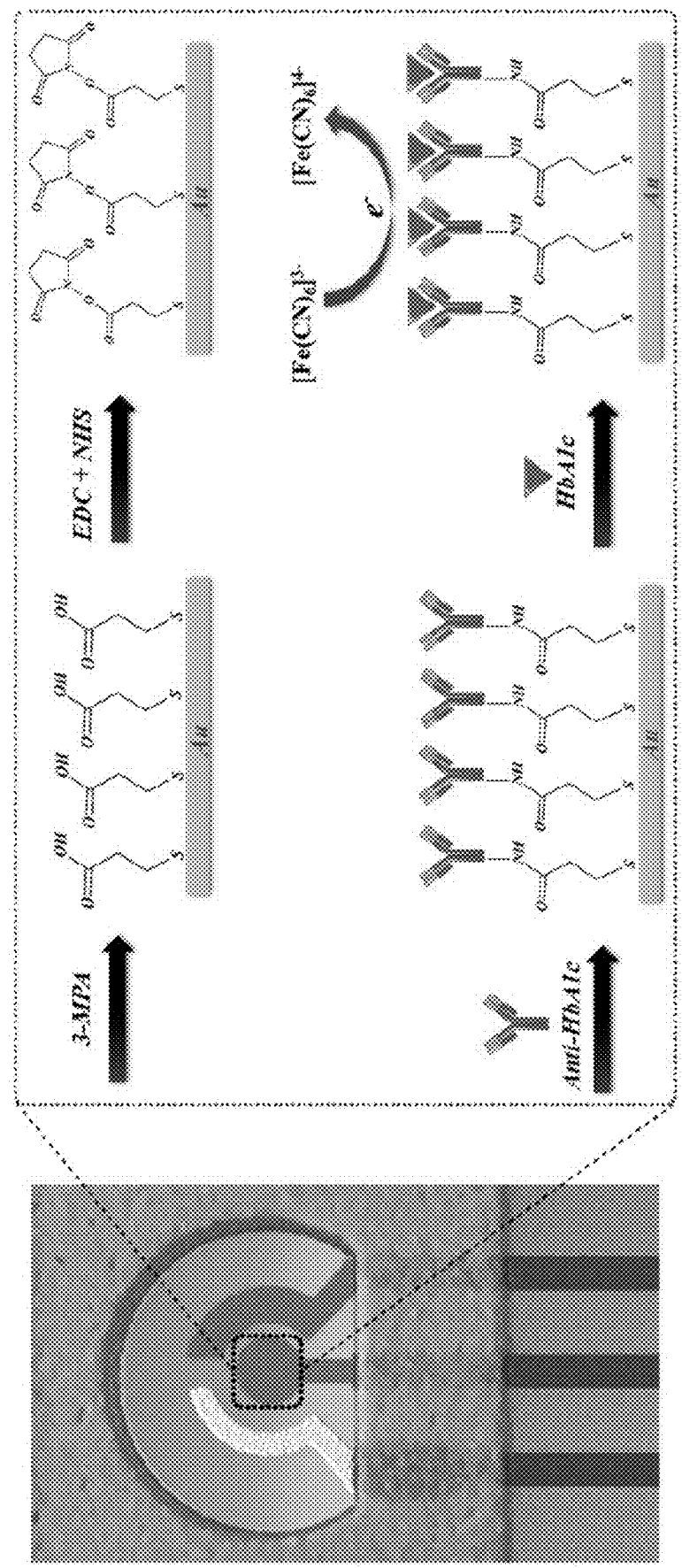
FIG. 2 is a schematic representation of the stepwise fabrication process of the immunosensor.

In this Example, we describe a single-use disposable thin-film gold-based working and counter electrodes were constructed as a label-free HbA1c biosensor. FIG. 2 shows a schematic representation of the fabrication steps of this biosensor. Anti-HbA1c was used as a selective HbA1c-capturing probe. Self-assembled monolayers of MPA were employed to covalently immobilize anti-HbA1c on the surface of the gold electrode. Differential pulse voltammetry (DPV) was employed as the electrochemical detection method to enhance the sensitivity through minimization of the charging current. Details of the fabrication processing of the biosensor will be given later.

Materials and Methods
Apparatus and Reagents

Phosphate Buffer Solution (PBS) 1.0 M (pH 7.4), human serum, 3-Mercaptopropionic acid (MPA), human hemoglobin, bovine serum albumin (BSA), N-(3-dimethylaminopropyl)-$N^1$-ethylcarbodiimide hydrochloride (EDC) and N-hydroxysuccinimide (NHS) were purchased from Sigma-Aldrich (St. Louis, Mo., USA). Human Hemoglobin A1c (HbA1c) and mouse anti-Human Hemoglobin A1c (anti-HbA1c) IgG1 were purchased from US Biological (Salem, Mich., USA). Potassium hydroxide pellets, concentrated $H_2SO_4$ 95.0 to 98.0 w/w % and concentrated $HNO_3$ 70% w/w % were received from Fisher Scientific (Pittsburgh, Pa., USA). All the chemicals were used without further purification. A CHI660C (CH Instrument, Inc., Austin, Tex., USA) Electrochemical Workstation was used for DPV and EIS investigations. All the experiments were conducted at room temperature. X-ray Photoelectron Spectroscopy (XPS) was performed by a PHI Versaprobe 5000 Scanning X-ray Photoelectron Spectrometer.

Electrode Fabrication

Figure 3:
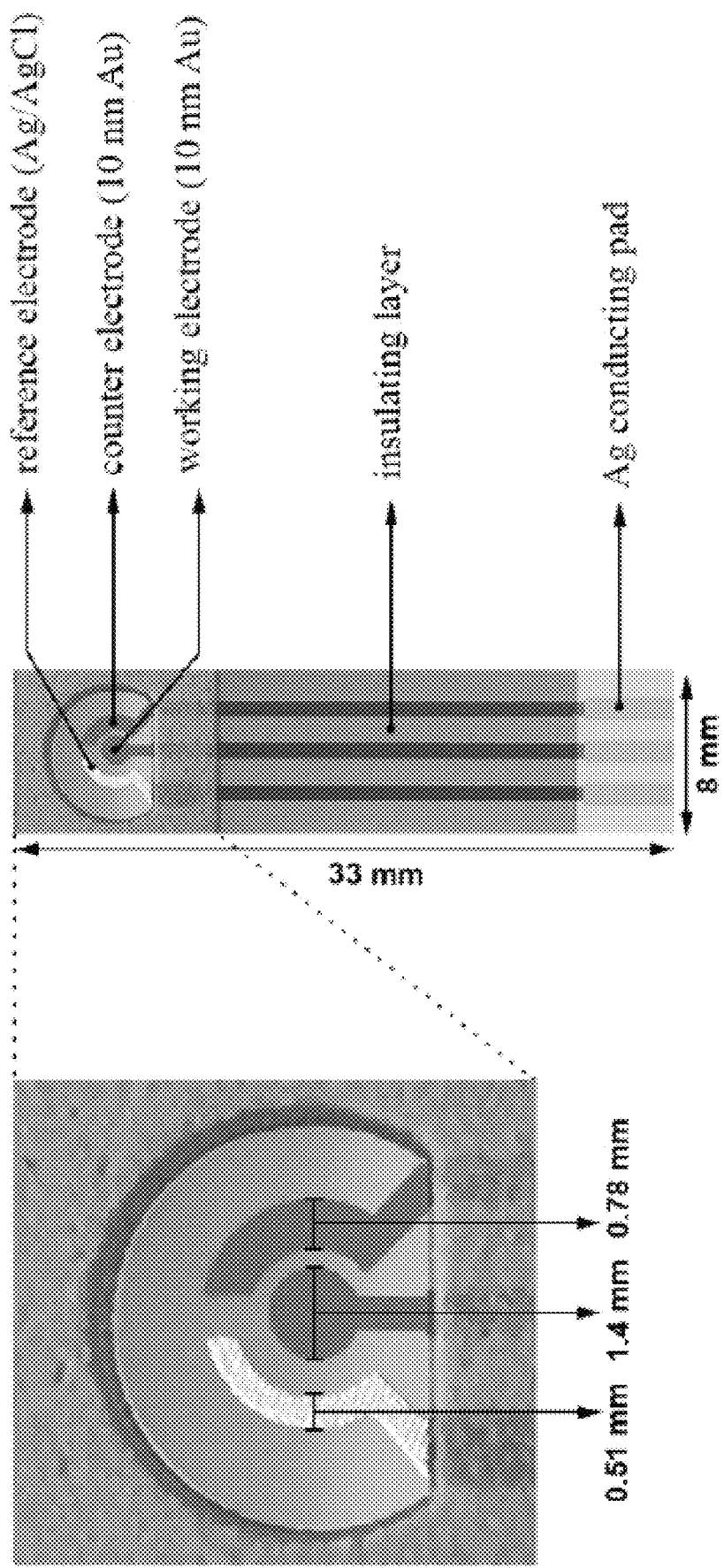
FIG. 3 illustrates structure and dimensions of the thin-film gold-based HbA1C biosensor prototype.

FIG. 3 shows the biosensor prototype and its actual dimensions used in this study. The conventional three-electrode configuration consisted of a 10-nm-thin gold film used as working and counter electrodes and a thick-film printed Ag/AgCl reference electrode. Thin gold film was deposited on polyethylene terephthalate (PET) by sputtering technique without any binder and the biosensor was patterned by laser ablation technique. Separate masks were used producing different elements of the biosensor prototype. The Ag/AgCl reference electrode and the insulation layer were thick-film printed using DuPont #5870 Ag/AgCl and Nazdar APL 34 silicone-free dielectric inks respectively. 100 individual biosensors in 4 rows were fabricated on each PET sheet (355 280 $mm^2$). The overall dimensions of an individual biosensor were 33.0 8.0 $mm^2$. The working electrode area was 1.54 $mm^2$ accommodating 10-15 μL of liquid test sample. The combination of sputtering and laser ablation techniques resulted in producing a very thin and yet uniform gold layer featuring high-reproduction and low-cost at the same time. This promising and unique fabrication technique allowed for mass production of single-use disposable biosensors. More detailed explanation of the electrode fabrication process can be found elsewhere.

Electrode Functionalization
Pretreatment of Gold Electrode (AuE)

A pretreatment procedure was applied to the gold electrode, prior to the MPA-SAM deposition. This three-step pretreatment procedure resulted in a significant decrease in electrode charge transfer resistance enhancing the reproducibility of the biosensor. A row of five or seven biosensors were immersed in a 2 M KOH solution for 15 min After rinsing with copious amount of DI water, the biosensors were placed in a 20-fold diluted concentrated $H_2SO_4$ solution (95.0 to 98.0 w/w %) for another 15 min. DI water was then used to rinse the biosensor prototypes. The biosensors were then placed in a 20-fold diluted concentrated HNO3 solution (70% w/w %) for another 15 min. The biosensors were rinsed once more time with DI water and dried in a steam of nitrogen. During this pretreatment procedure, the counter and the reference electrodes were not covered. Concentrations of acids and base solutions used in this pretreatment procedure were optimized to be effective while maintained the integrity of the thin gold film working and counter electrodes and the Ag/AgCl reference electrode as well as the overall structure of the biosensor. The effectiveness of the pretreatment procedure was assessed using EIS and the results were excellent.

Anti-HbA1c Immobilization on AuE

In all the electrode surface modification steps, both the counter and the reference electrodes were not covered resulting to a more practical and fast surface modification protocol. Typically, a row of five biosensors were subjected at once to surface modification. Self-assembled monolayers of MPA were exploited to wire the anti-HbA1c to the surface of gold working electrode. MPA molecule consisted of a thiol functional group at one end which processed a great affinity to gold and a carboxylic group at another end which was suitable for bonding covalently to proteins through peptide bond after an activation procedure. Thiol modification of gold electrode surface for protein immobilization was a well-developed technique. The biosensor used in this study was immersed in 1 mM solution of MPA in ethanol for 24 h in dark, rinsed with DI water and dried in a steam of $N_2$. The MPA modified AuEs were incubated in 0.1 M PBS (pH=7.4) containing 0.25 M EDC and 0.05 M NHS for 5 h to activate MPA carboxylic groups. Activated AuEs were then rinsed by 0.1 M PBS and dried by $N_2$ flow. 5 μL of 0.05 mg/mL anti-HbA1c was casted on the sensing area of each AuE and left to dry overnight at 4° C. Antibody immobilized biosensors were rinsed with 0.1 M PBS and immersed in 1% BSA solution in 0.1 M PBS for 1 h to prevent non-specific bonding. The biosensors were then rinsed with 0.1 M PBS, dried under a steam of $N_2$ and stored at 4° C.

Electrochemical Measurements

Figure 4:
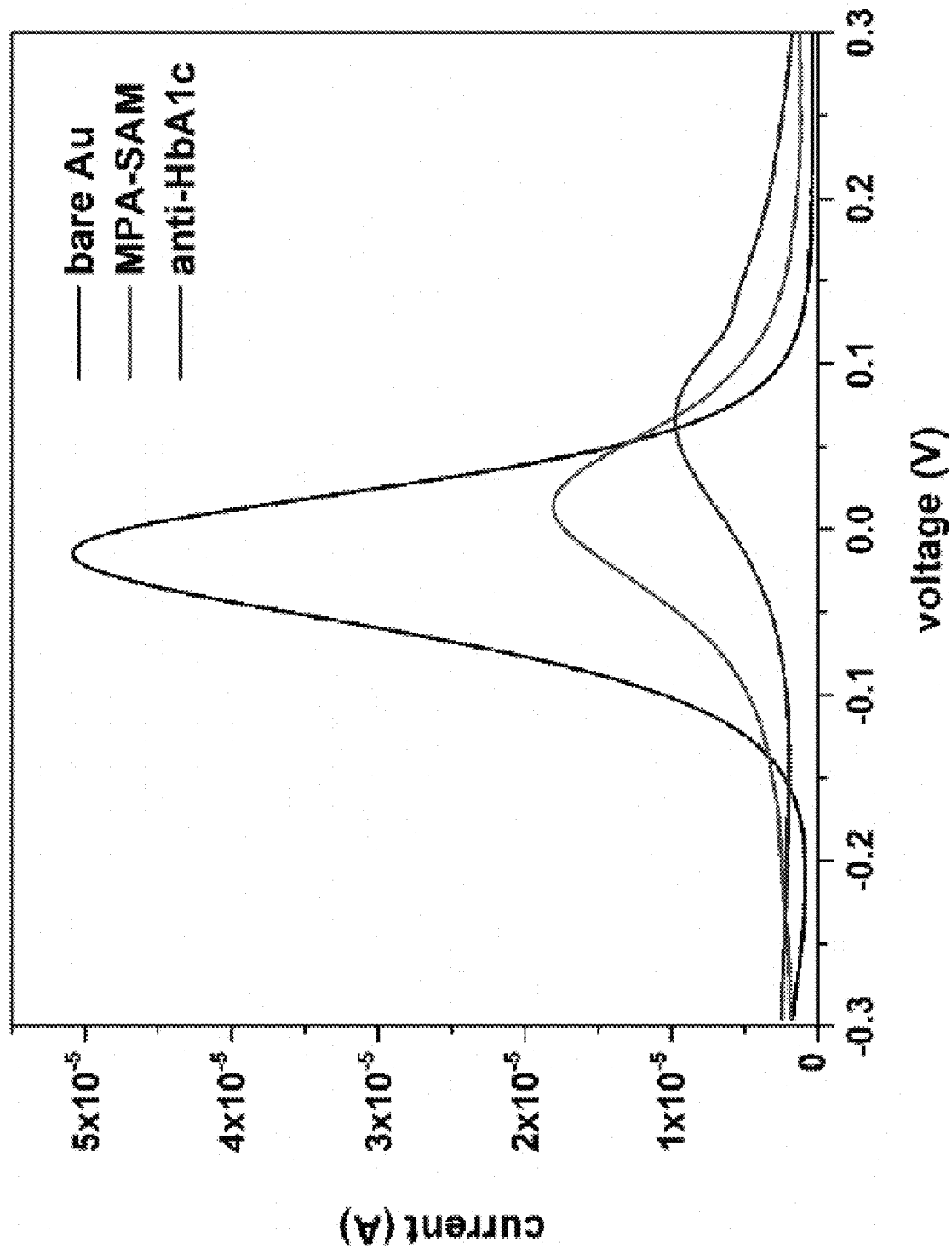
FIG. 4 illustrates gradual decrease in the signal generated by $K_3Fe(CN)_6/K_4Fe(CN)_6$ redox couple reaction as a result of MPA-SAM formation and anti-HbA1c (50 µg/mL in 0.1 M PBS) immobilization on the surface of gold electrode.
Figure 5A:
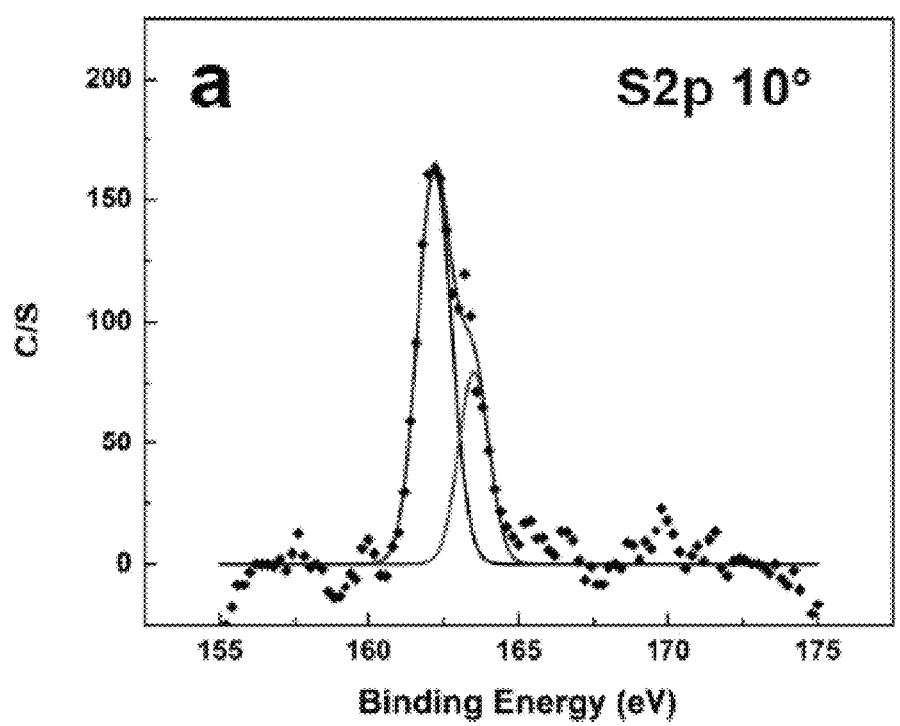
FIGS. 5(A-F) illustrate high resolution spectra of C(1s) and S(2p) obtained for MPA-SAM-modified AuE at take-off angles of 10°, 50° and 90°.
Figure 5B:
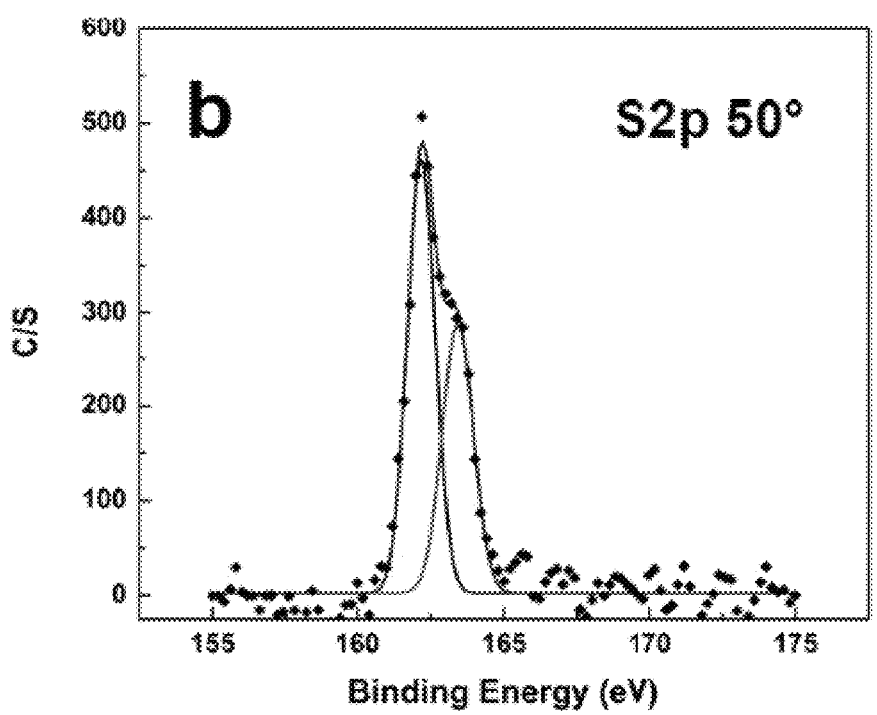
Figure 5C:
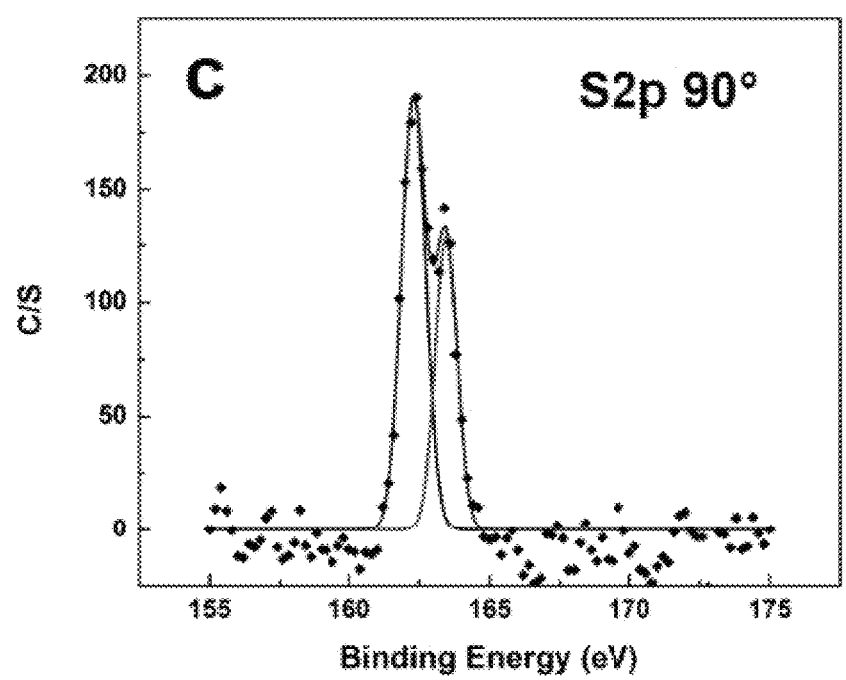
Figure 5D:
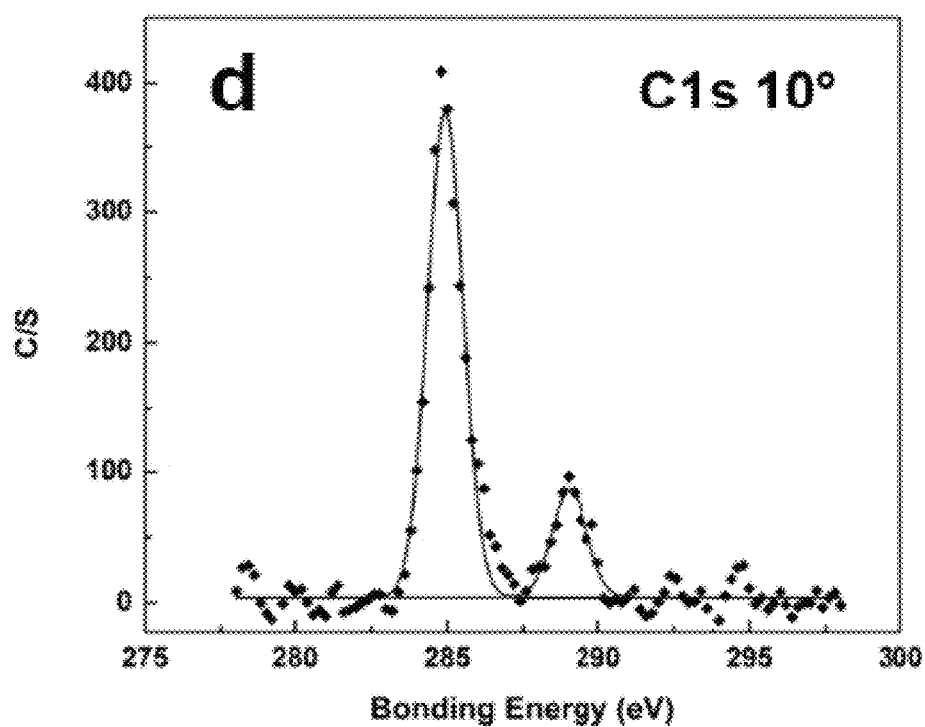
Figure 5E:
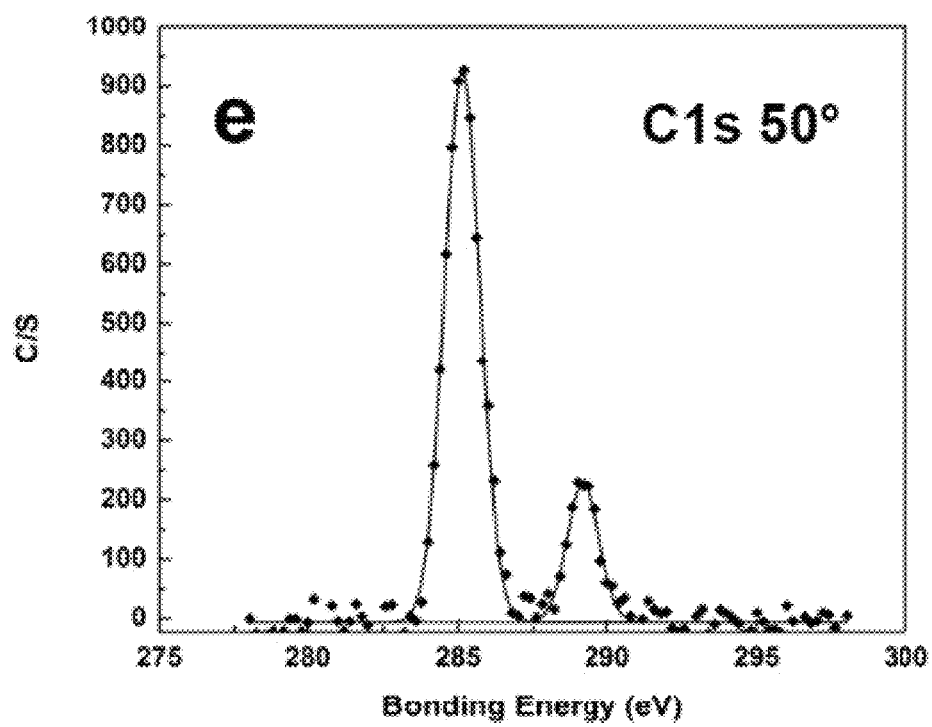
Figure 5F:
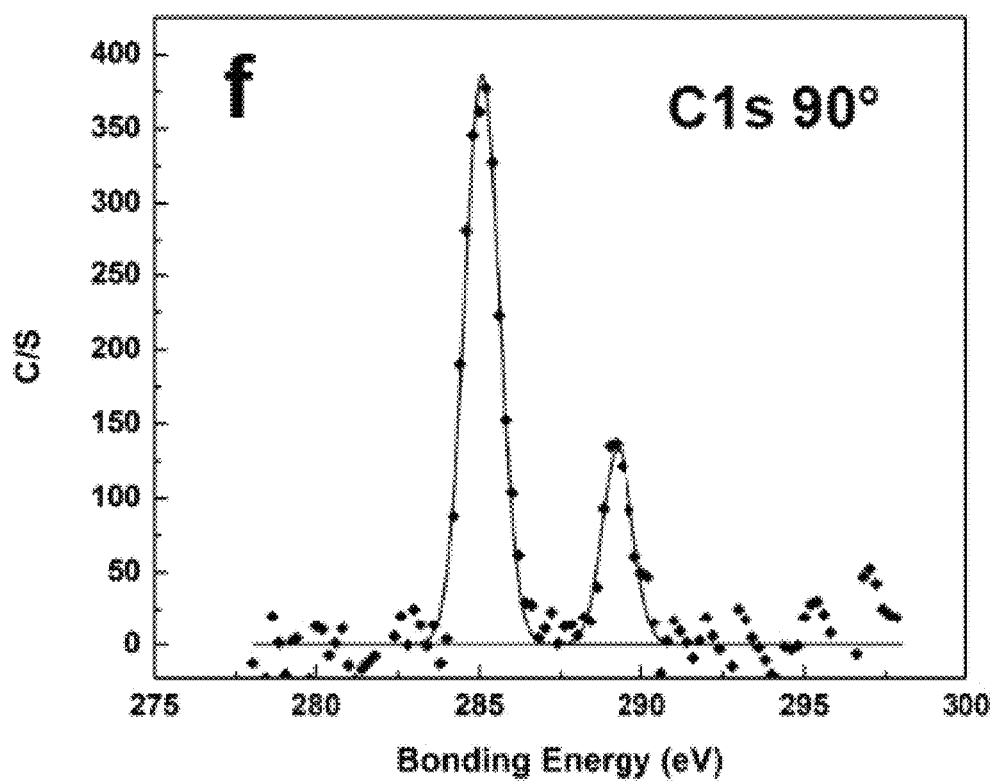

The experimental measurements were performed at ambient temperature. A solution of $K_3Fe(CN)_6$ and $K_4Fe(CN)_6$, with 5 mM in each component, was prepared in 0.1 M PBS and used as the redox coupled probe for DPV and EIS tests. EIS tests were performed in frequency range of $10^{-2}$ to $10^4$ Hz with 5 mV voltage amplitude. Randles equivalent circuit models were used to fit the Nyquist plots of EIS using EC-lab standard software. Anti-HbA1c immobilized AuEs were rinsed with 0.1 M PBS and dried in a stream of $N_2$. 5 μL of HbA1c of selected concentration was pipetted on the sensing area of AuE and allowed to be dried for 2 h at room temperature. The biosensor was then rinsed with 0.1 M PBS. DPV and EIS measurements were performed after drop casting of 20 μL $K_3Fe(CN)_6/K_4Fe(CN)_6$ redox couple solution on the sensing area of AuE. EIS was used to investigate the surface coverage of MPA-SAM formed on AuE. The electron transfer reaction associated with ferricyanide/ferrocyanide redox couple transformation can be hindered by the presence of bulky moieties on the surface of the electrode. FIG. 4 presents the gradual decrease in the signal generated by $K_3Fe(CN)_6/K_4Fe(CN)_6$ redox couple reaction as a result of MPA-SAM formation and Anti-HbA1c immobilization on the surface of gold electrode. Therefore, the hindering effect of HbA1c on ferricyanide/ferrocyanide electron transfer reaction was exploited as HbA1c detection mechanism.

X-Ray Photoelectron Spectroscopy

The interaction between the MPA-SAM thiol groups and thin gold film electrode was investigated using X-ray photoelectron spectroscopy (XPS). The pretreated biosensor was immersed in 1 mM solution of MPA in ethanol for 24 h in dark, and then rinsed with DI water and dried in a stream of nitrogen. High resolution C(1s) and S(2p) spectra were collected using a monochromatic Al Kα X-ray source at the take-off angles of 10°, 50° and 90°. High resolution C(1s) spectra was used to assess the orientation of MPA-SAM molecules formed on AuE. The atomic ratio between MPA carboxylic group carbon (O—C=O) and the carbons from MPA hydrocarbon backbone (C—C) was calculated at each take-off angle and compared to verify the upward orientation of MPA-SAM.

Results and Discussion

MPA-SAM Characterization

X-Ray Photoelectron Spectroscopy

FIG. 5 shows XPS high resolution spectra of C(1s) and S(2p) obtained for MPA-SAM-modified AuE at the take-off angles of 10°, 50° and 90°. The higher energy peak in S(2p) spectra was at 163.5 eV as presented in FIG. 5A-C, representing the characteristic of the free thiol group (—SH). As a result of the Au—S covalent bond, the S(2p) peak was shifted by 1.5 eV negative of the 163.5 eV. Our results agreed exceptionally well with other reported research. Thus, the higher intensity peak at 162 eV in FIG. 5A-C confirmed the formation of the covalent bond between the MPA-SAM thiol groups and AuE. Furthermore, the relative intensity of the free thiol groups to covalently bonded thiol groups increased by increasing the take-off angle from 10° to 90°, as shown in FIG. 5A-C. This indicated that by approaching toward the surface of the gold electrode, the number of free thiol groups appeared to decrease. The lower energy peak at the C(1s) spectra (285 eV) in FIG. 5D-F was characteristic of saturated hydrocarbons (C—C) which could be assigned to carbons participating in the MPA backbone. The lower intensity peak at 288.9 eV in the C(1s) spectra was associated with —COOH. Table 1 presents the atomic ratio between the MPA carboxylic group carbon (O—C=O) and the carbons from the MPA hydrocarbon backbone (C—C) at different take-off angles. This was calculated by the peak integration of the C(1s) spectra. As shown in Table 1, the relative number of carbons participating in the carboxylic groups decreased with decreasing the take-off angle from 90° to 10°. Thus, there were fewer numbers of carboxylic groups near the surface. This observation confirmed the upward orientation of MPA-SAM carboxylic groups in this MPA-SAM arrangement.

TABLE 1

Atomic ratio between MPA carboxylic group carbon (O—C=O) and the carbons from the MPA hydrocarbon backbone (C—C) at different take-off angles

| Take-off | —COOH | O—C=O | —COOH/O—C=O |
|---|---|---|---|
| 10° | 122.20 | 547.62 | 0.2231 |
| 50° | 330.02 | 1385.55 | 0.2382 |
| 90° | 164.08 | 516.98 | 0.3174 |

EIS Assessment of MPA-SAM Surface Coverage

FIG. 6a presents the electrochemical impedance spectroscopy (EIS) results for the bare and MPA-SAM-modified gold electrodes in the frequency range of $10^{-2}$ to $10^4$ Hz with a 5 mV voltage amplitude in the form of a Nyquist plot. FIG. 6B shows the Randles equivalent circuit used to model the experimental data. Each component in the equivalent circuit represented an element in the physical electrode/electrolyte interface. The semicircular region of the Nyquist plot was associated with the electron transfer process which was modeled by a parallel circuit representation of a resistor (Rct) and a capacitor (Q). The tail at the lower frequencies indicated the presence of a diffusion-limited electrochemical process, which was represented using the Warburg element (Zw). The solution resistance was represented by Rs. The electrode charge transfer resistance (Rct) was related to the MPA-SAM surface coverage assuming that the electron transfer reaction occurred only at uncovered spots and that the diffusion to these defects is planar. The MPA-SAM surface coverage ratio was then calculated using the following equations:

$$\theta_{IS}^R = 1 \left( \frac{R_{ct}^{AuR}}{R_{ct}^{SAM}} \right)$$

where $R_{ct}^{AuE}$ and $R_{ct}^{SAM}$ are charge transfer resistances measured at bare and MPA-SAM-covered electrodes, respectively. When $\theta_{15}^R > 0.9$, the surface coverage fraction could be evaluated using a model based on pinhole size:

$$\theta_{IS}^R = 1 - \left(\frac{\sigma_\omega}{m - \sigma_\omega}\right)$$

where σw is the Warburg coefficient (slop of Z' vs. $\omega^{-1/2}$ plot obtained for bare AuE) and m is the slope of the linear interval in the high frequency region of the Z' vs. $\omega^{-1/2}$ plot obtained at MPA-SAM-modified AuE. Table 2 presents data obtained from the Randles equivalent circuit modeling of EIS Nyquist plots for bare and monolayer-covered electrodes. The calculated value of θP=0.9950 for MPA monolayers indicated a high coverage fraction compared to previous reports.

TABLE 2

Data obtained from Randles equivalent circuit modeling of EIS Nyquist plots for bare and monolayer-covered electrodes

| Surface | Q(uF) | $Z_w$ (Ω) | $\sigma_w$ ($\Omega \cdot s^{-1/2}$) | m | $R_{ct}$ (Ω) | $R_S$ (Ω) | $\theta_{IS}^R$ | $\theta_{IS}^P$ |
|---|---|---|---|---|---|---|---|---|
| bare AuE | 1.31 | 972.6 | 367.7 | | 201.5 | 107 | | |
| MPA-SAM | 0.46 | 1738 | | 74,542 | 10,347 | 152 | 0.9805 | 0.9950 |

The high surface coverage of MPA-SAM together with the formation of the Au—S covalent bond and the upward orientation of the MPA carboxylic groups suggested that our immobilization process of anti-HbA1c on the MPA-SAM-modified gold electrode was very effective.

HbA1c Detection Using Differential Pulse Voltammetry (DPV)

The MPA-SAM-modified gold electrode was successfully characterized, and the HbA1c biosensor was ready for the evaluation of its performance Cyclic voltammetry and amperometry are the two most used electrochemical detection techniques. However, differential pulse voltammetry (DPV) provides a linear sweep voltammetry with a series of regular voltage pulses superimposed on the linear potential sweep. Consequently, the current is measured immediately before each potential change. Thus, the effect of the charging current is minimized, achieving a higher sensitivity. Hence, in this study, we used DPV measurement to achieve higher sensitivity compared to cyclic voltammetry and amperometry.

HbA1c Detection in 0.1 M PBS

Figure 7A:
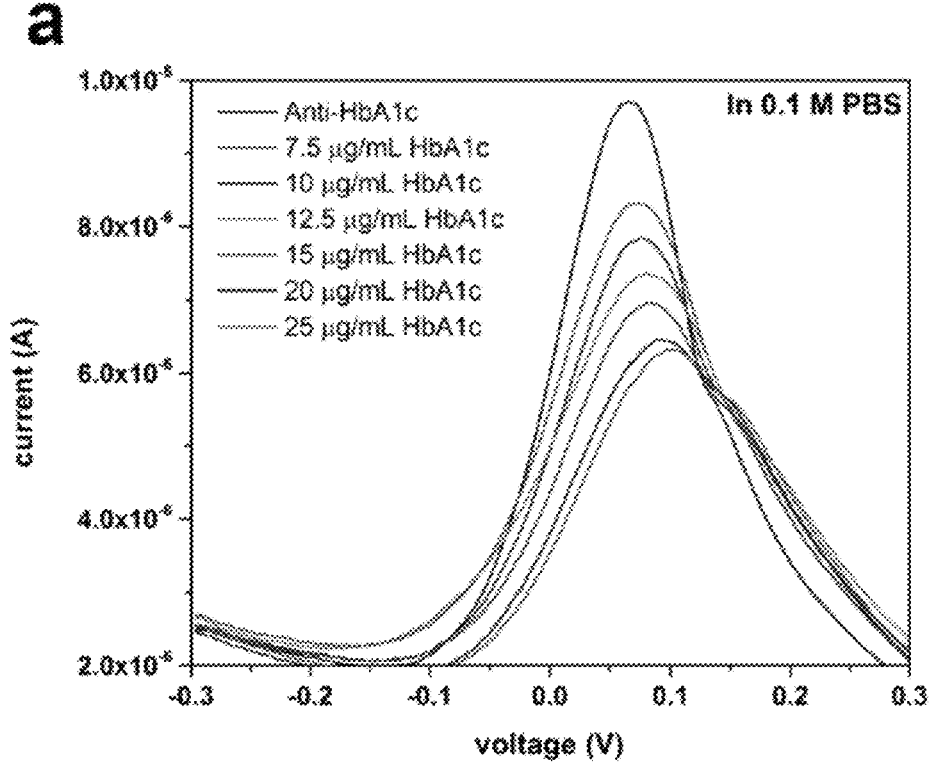
FIGS. 7A-B illustrate (A) DPV measurement of HbA1c antigen in 0.1 M PBS in the concentration range of 7.5-25 µg/mL using 5 µL of 0.05 mg/mL anti-HbA1c as a detection probe; (B) Calibration curve of HbA1c antigen concentration using the peak current output of the biosensor obtained from results of FIG. 7A (n=4).
Figure 7B:
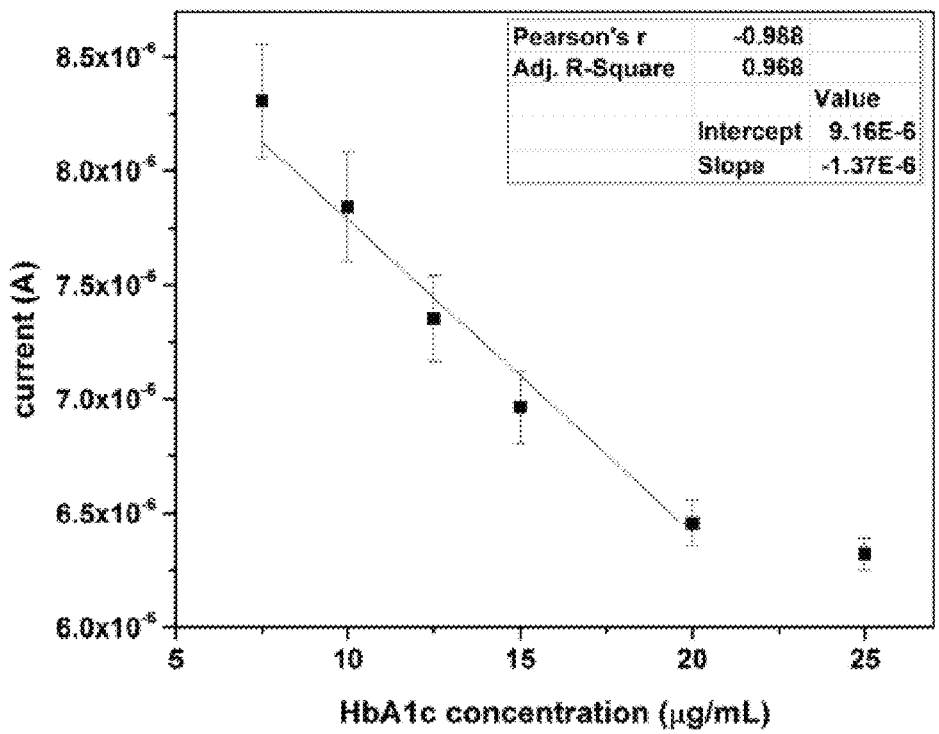

FIG. 7a shows the testing results of our HbA1c biosensor in 0.1 M PBS test medium over an HbA1c concentration range of 7.5-25 μg/mL. The DPV of the anti-HbA1c casted biosensor without HbA1c antigen was measured as the baseline. Each biosensor was used once for testing each HbA1c concentration, aimed at single-use disposable in vitro applications. Multiple test runs were carried out with n>3. As can be seen in FIG. 7a, there is a gradual decrease in the signal generated by the ferricyanide/ferrocyanide transformation reaction as a result of the increasing HbA1c concentration. This is due to the electron transfer hindering effect of the antigen which was captured on the surface of the anti-HbA1c immobilized gold electrode. FIG. 7b is the calibration curve of HbA1c measurement in 0.1 M PBS test medium based on the testing results from FIG. 7A. An acceptable correlation coefficient of 0.968 was obtained for the biosensor in the range of 7.5-20 μg/mL. As such, 7.5 μg/mL was the lowest detection limit for the biosensor in 0.1 M PBS testing medium as the sensor's responses to antigen concentrations less than 7.5 μg/mL were not reproducible.

HbA1c Detection in Undiluted Human Serum

Figure 8A:
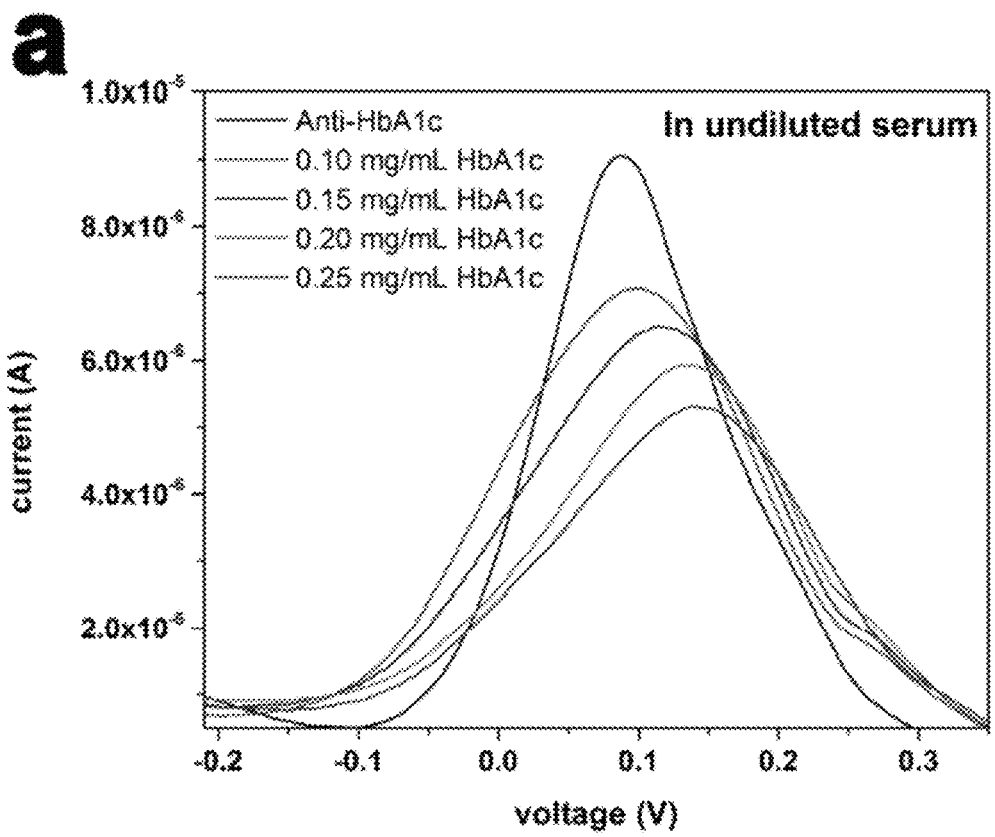
FIGS. 8A-B illustrates (A) DPV measurement of HbA1c antigen in serum in the concentration range of 0.10-0.25 mg/mL using 5 µL of 0.5 mg/mL anti-HbA1c as the detection probe of the biosensor; (B) Calibration curve of HbA1c antigen concentration in serum using the peak current output of the biosensor obtained from results of FIG. 7A (n=4).
Figure 8B:
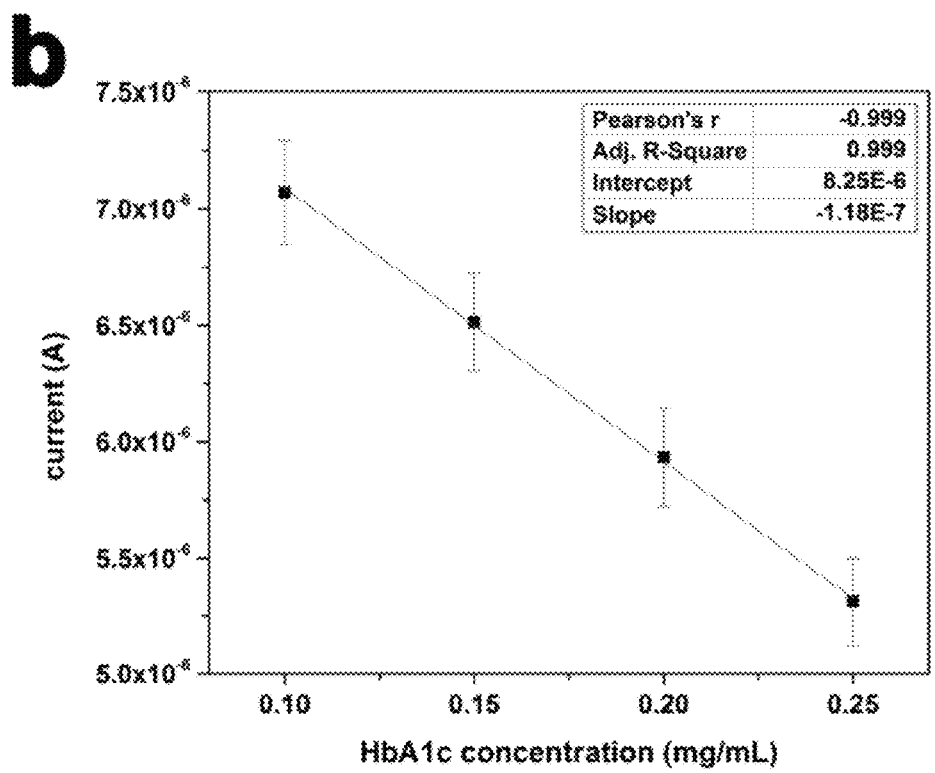

HbA1c measurements were performed in undiluted human serum to show the potential application of the sensor in real blood samples. Considering the normal adult human hemoglobin (HbA10) concentration of 150 mg/mL, the HbA1c concentration for a diabetic patient (6.5% HbA1c) is more than 9 mg/mL in whole blood. Samples with an HbA1c concentration range of 0.1-0.25 mg/mL were prepared in undiluted human serum which were 10 times higher than the ones that were tested in 0.1 M PBS, and these was more clinically relevant. The antibody concentration for the biosensors tested in serum was 0.5 mg/mL in 0.1 M PBS. FIG. 8a shows the DPV measurements of the HbA1c antigen in undiluted serum over the concentration range of 0.10-0.25 mg/mL and it also includes the measurement of 0 mg/mL HbA1c serving as the baseline.

The biosensors for the measurement of HbA1c in serum were used only once for each HbA1c concentration to accomplish the goal of developing a single-use disposable in vitro HbA1c biosensor. FIG. 7A,B exhibit the excellent performance of the biosensor for HbA1c detection in serum. The correlation coefficient for linear fitting was 0.999. Measurements of the HbA1c antigen in serum at the concentration level of μg/mL were also undertaken (data not presented). The DPV measurement of the HbA1c antigen in serum at the level of 15-25 μg/mL was good and meaningful. However, the repeatability of the DPV measurements at lower HbA1c antigen concentrations <10 μg/mL were only fair. This might be the lowest detection limit of HbA1c in serum. Nevertheless, the DPV measurements of HbA1c in undiluted serum over the range of 0.10-0.25 mg/mL demonstrated this potential application of the biosensor in diabetic management.

A single-use disposable in vitro HbA1c biosensor was designed, fabricated and produced in a cost-effective manner. The interaction between anti-HbA1c and its antigen (the analyte) was the bio-recognition mechanism of this biosensor. Differential pulse voltammetry (DPV) was employed as the transduction mechanism for this biosensor. Covalent immobilization of anti-HbA1c onto the gold thin-film electrode was accomplished by MPA-SAM modification. Confirmation of the thiol group bonding on the gold-based electrode elements and the upward orientation of the MPA-SAM carboxylic groups were experimentally assessed. Excellent coverage and upward orientation of the MPA-SAM was obtained. DPV measurements of HbA1c in 0.1 M PBS test medium in the range of 7.5-20 μg/mL and in serum in the range of 0.1-0.25 mg/mL were carried out. The results were excellent. This research suggested that a cost-effective, single-use, disposable in vitro HbA1c biosensor could be used alone or together with a blood glucose biosensor for better diabetic management applications.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention the following is claimed:

1. A detection system for detecting HbA1c levels in a sample, the system comprising:
    a sensor that includes a substrate, a gold working electrode formed on a surface of the substrate; a counter electrode formed on the surface of the substrate; a dielectric layer covering a portion of the gold working electrode and counter electrode and defining an aperture exposing other portions of the gold working electrode and counter electrode; and an anti-HbA1c antibody functionalized or chemically functionalized to a surface of the exposed portion of the gold working electrode with a monolayer consisting of 3-mercaptopropionic acid (MPA), the anti-HbA1c antibody selectively binding to, respectively, βHbA1c in a sample and the HbA1c once bound being detectable by measuring the current flow between the gold working electrode and the counter electrode,
    a redox solution that is applied to the gold working electrode for determining the quantity of HbA1c in the sample bound, respectively, to the anti-HbA1c antibody, and
    a measuring device for applying voltage potentials to the gold working electrode and the counter electrode and measuring the current flow between the gold working electrode and the counter electrode.

2. The system of claim 1, wherein the working electrode and the counter electrode comprise metalized films.

3. The system of claim 2, wherein the counter electrode comprises one of gold, platinum, palladium, silver, carbon, alloys thereof, and composites thereof.

4. The system of claim 2, wherein the metalized films are provided on the surface of the substrate by sputtering or coating the films on the surface and wherein the working electrode and the counter electrode are formed using laser ablation to define the dimensions of the working electrode and the counter electrode.

5. The system of claim 1, wherein the redox solution comprises potassium ferrocyanide/potassium ferricyanide solution.

6. The system of claim 1, further comprising a reference electrode on the surface of the substrate, the dielectric covering a portion of the reference electrode.

7. The system of claim 1, wherein the sample comprises blood or serum.

8. The system of claim 1, wherein the 3-MPA monolayer is coated directly onto the working electrode surface.

9. A detection system for detecting HbA1c levels in a sample, the system comprising:
    a sensor that includes a substrate, a gold working electrode formed on a surface of the substrate; a counter electrode formed on the surface of the substrate; a dielectric layer covering a portion of the gold working electrode and the counter electrode and defining an aperture exposing other portions of the gold working electrode and the counter electrode; and
    an anti-HbA1c antibody functionalized or chemically functionalized to a surface of the exposed portion of the gold working electrode with a monolayer consisting of 3-mercaptopropionic acid (MPA), the anti-HbA1c antibody selectively binding to, respectively, HbA1c in a sample and the HbA1c once bound being detectable by measuring the current flow between the gold working electrode and the counter electrode,
    an equimolar potassium ferrocyanide/potassium ferricyanide redox solution that is applied to the gold working electrode for determining the quantity of HbA1c in the sample bound to, respectively, the anti-HbA1c antibody, and
    a measuring device for applying voltage potentials to the gold working electrode and the counter electrode and measuring the current flow between the gold working electrode and the counter electrode.

10. The system of claim 9, wherein the working electrode and the counter electrode comprise metalized films.

11. The system of claim 10, wherein the metalized films are provided on the surface of the substrate by sputtering or coating the films on the surface and wherein the working electrode and the counter electrode are formed using laser ablation to define the dimensions of the working electrode and the counter electrode.

12. The system of claim 10, wherein the sample comprises blood or serum.

13. The system of claim 9, wherein the counter electrode comprises one of gold, platinum, palladium, silver, carbon, alloys thereof, and composites thereof.

14. The system of claim 9, further comprising a reference electrode on the surface of the substrate, the dielectric covering a portion of the reference electrode.

15. A detection system for detecting HbA1c levels in a sample, the system comprising:
    a sensor that includes a substrate, a gold working electrode formed on a surface of the substrate; a counter electrode formed on the surface of the substrate; a dielectric layer covering a portion of the gold working electrode and the counter electrode and defining an aperture exposing other portions of the gold working electrode and the counter electrode; and an anti-HbA1c antibody functionalized or chemically functionalized to a surface of the exposed portion of the gold working electrode with a monolayer consisting of 3-mercaptopropionic acid (MPA) coated directly onto the gold working electrode surface, the anti-HbA1c antibody selectively binding to HbA1c in a sample and the HbA1c once bound being detectable by measuring the current flow between the gold working electrode and the counter electrode,
    an equimolar potassium ferrocyanide/potassium ferricyanide redox solution that is applied to the gold working electrode for determining the quantity of HbA1c in the sample bound to the anti-HbA1c antibody, and
    a measuring device for applying voltage potentials to the gold working electrode and the counter electrode and measuring the current flow between the gold working electrode and the counter electrode.

16. The system of claim 15, wherein the working electrode and the counter electrode comprise metalized films, the metalized films are provided on the surface of the substrate by sputtering or coating the films on the surface and wherein the working electrode and the counter electrode are formed using laser ablation to define the dimensions of the working electrode and the counter electrode.

17. The system of claim 15, wherein the sample comprises blood.

* * * * *